(12) United States Patent
Prinzen et al.

(10) Patent No.: US 9,248,294 B2
(45) Date of Patent: Feb. 2, 2016

(54) METHOD AND APPARATUS FOR OPTIMIZATION OF CARDIAC RESYNCHRONIZATION THERAPY USING VECTORCARDIOGRAMS DERIVED FROM IMPLANTED ELECTRODES

(71) Applicant: Medtronic, Inc., Minneapolis, MN (US)

(72) Inventors: Frits W Prinzen, Maastricht (NL); Elien Engels, Maastricht (NL); Alfonso Aranda Hernandez, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/023,791

(22) Filed: Sep. 11, 2013

(65) Prior Publication Data

US 2015/0073286 A1  Mar. 12, 2015

(51) Int. Cl.
*A61N 1/365* (2006.01)
*A61B 5/04* (2006.01)
*A61N 1/362* (2006.01)
*A61N 1/368* (2006.01)

(52) U.S. Cl.
CPC ............ *A61N 1/365* (2013.01); *A61B 5/04011* (2013.01); *A61N 1/3627* (2013.01); *A61N 1/3684* (2013.01); *A61N 1/3686* (2013.01); *A61N 1/36507* (2013.01)

(58) Field of Classification Search
None
See application file for complete search history.

(56) References Cited

U.S. PATENT DOCUMENTS

| | | | |
|---|---|---|---|
| 5,843,141 A | 12/1998 | Bischoff et al. | |
| 5,954,660 A | 9/1999 | Legay et al. | |
| 6,178,344 B1 | 1/2001 | Hull et al. | |
| 6,370,423 B1 | 4/2002 | Guerrero et al. | |
| 6,567,704 B2 | 5/2003 | Sundquist et al. | |
| 6,643,549 B1 * | 11/2003 | Bradley et al. | 607/28 |
| 6,743,227 B2 | 6/2004 | Seraj et al. | |
| 6,799,991 B2 | 10/2004 | Williams et al. | |
| 6,854,994 B2 | 2/2005 | Stein et al. | |
| 6,901,289 B2 | 5/2005 | Dahl et al. | |
| 6,968,235 B2 | 11/2005 | Belden et al. | |
| 6,978,178 B2 | 12/2005 | Sommer et al. | |
| 7,076,309 B2 | 7/2006 | Hine et al. | |
| 7,087,017 B2 | 8/2006 | Christopherson et al. | |
| 7,092,759 B2 | 8/2006 | Nehls et al. | |
| 7,107,093 B2 | 9/2006 | Burnes | |
| 7,139,610 B2 * | 11/2006 | Ferek-Petric | A61N 1/36185 607/27 |
| 7,239,916 B2 | 7/2007 | Thompson et al. | |
| 7,254,450 B2 | 8/2007 | Christopherson et al. | |
| 7,287,995 B2 | 10/2007 | Stein et al. | |
| 7,532,939 B2 | 5/2009 | Sommer et al. | |
| 7,558,626 B2 * | 7/2009 | Corbucci | 607/9 |
| 7,623,053 B2 | 11/2009 | Terry et al. | |

(Continued)

OTHER PUBLICATIONS

"Vectorcardiography as a tool for easy optimization of cardiac resynchronization in canine LBBB hearts"; Van Deursen, et al, Circ. Arrhythm. Electrophysiol, 2012; 5:544-522.

(Continued)

*Primary Examiner* — Brian T Gedeon
(74) *Attorney, Agent, or Firm* — Carol F. Barry

(57) ABSTRACT

A cardiac resynchronization pacemaker and a method of adjusting the pacemaker. The method includes deriving a vectorcardiogram from implanted electrodes (D-VCG), analyzing the D-VCG, deriving optimal CRT pacing parameters from the analysis of the D-VCG, and adjusting the CRT pacemaker according to the derived parameters. The pacemaker may include a processor configured to perform the method.

25 Claims, 12 Drawing Sheets

(56) References Cited

U.S. PATENT DOCUMENTS

| | | | |
|---|---|---|---|
| 7,672,733 B2 | 3/2010 | Zhou et al. |
| 7,783,365 B2 | 8/2010 | Ebert et al. |
| 7,846,095 B2 | 12/2010 | Christopherson et al. |
| 8,005,544 B2 * | 8/2011 | Zhu et al. .......................... 607/9 |
| 8,019,420 B2 | 9/2011 | Hine et al. |
| 8,065,008 B2 | 11/2011 | Sommer et al. |
| 8,086,200 B2 | 12/2011 | Sutton et al. |
| 8,209,032 B2 | 6/2012 | Ebert et al. |
| 8,214,045 B2 | 7/2012 | Kronich et al. |
| 8,233,994 B2 | 7/2012 | Sommer et al. |
| 8,295,943 B2 | 10/2012 | Eggen et al. |
| 8,326,418 B2 | 12/2012 | Sommer et al. |
| 8,332,045 B2 | 12/2012 | Sommer et al. |
| 8,417,337 B2 | 4/2013 | Busacker et al. |
| 8,428,528 B2 | 4/2013 | Sutton et al. |
| 8,437,856 B2 | 5/2013 | Sommer et al. |
| 8,509,893 B2 | 8/2013 | Xiao et al. |
| 8,587,426 B2 | 11/2013 | Bloem |
| 8,615,298 B2 | 12/2013 | Ghosh et al. |
| 8,630,719 B2 | 1/2014 | Eggen et al. |
| 8,639,340 B2 | 1/2014 | Sommer et al. |
| 8,639,341 B2 | 1/2014 | Sommer et al. |
| 8,825,180 B2 | 9/2014 | Bauer et al. |
| 9,037,237 B2 | 5/2015 | Fischer et al. |
| 2001/0044624 A1 | 11/2001 | Seraj et al. |
| 2002/0077685 A1 | 6/2002 | Sundquist et al. |
| 2002/0111662 A1 | 8/2002 | Iaizzo et al. |
| 2002/0111663 A1 | 8/2002 | Dahl et al. |
| 2002/0173785 A1 | 11/2002 | Spear et al. |
| 2003/0018364 A1 | 1/2003 | Belden et al. |
| 2003/0018369 A1 | 1/2003 | Thompson et al. |
| 2003/0077935 A1 | 4/2003 | Stein et al. |
| 2003/0083586 A1 * | 5/2003 | Ferek-Petric ................ 600/512 |
| 2003/0204234 A1 | 10/2003 | Hine et al. |
| 2003/0216800 A1 | 11/2003 | Ebert et al. |
| 2004/0078067 A1 | 4/2004 | Thompson et al. |
| 2004/0087847 A1 | 5/2004 | Christopherson et al. |
| 2004/0176822 A1 | 9/2004 | Thompson et al. |
| 2004/0199082 A1 | 10/2004 | Ostroff et al. |
| 2004/0215252 A1 | 10/2004 | Verbeek et al. |
| 2004/0215299 A1 | 10/2004 | Zhao et al. |
| 2005/0020895 A1 | 1/2005 | Christopherson et al. |
| 2005/0021120 A1 | 1/2005 | Christopherson et al. |
| 2005/0033371 A1 | 2/2005 | Sommer et al. |
| 2005/0065570 A1 | 3/2005 | Stein et al. |
| 2006/0229693 A1 | 10/2006 | Bauer et al. |
| 2007/0299490 A1 | 12/2007 | Yang et al. |
| 2008/0039900 A1 | 2/2008 | Stein et al. |
| 2009/0054936 A1 | 2/2009 | Eggen et al. |
| 2009/0054941 A1 | 2/2009 | Eggen et al. |
| 2009/0054946 A1 | 2/2009 | Sommer et al. |
| 2009/0079606 A1 | 3/2009 | Terry et al. |
| 2009/0131873 A1 | 5/2009 | Spear et al. |
| 2009/0177110 A1 | 7/2009 | Lyden et al. |
| 2009/0192581 A1 | 7/2009 | Sommer et al. |
| 2009/0234405 A1 | 9/2009 | Sommer et al. |
| 2009/0234412 A1 | 9/2009 | Sambelashvili |
| 2009/0234414 A1 | 9/2009 | Sambelashvili et al. |
| 2009/0276004 A1 | 11/2009 | Kronich et al. |
| 2009/0306752 A1 | 12/2009 | Ebert et al. |
| 2010/0113943 A1 | 5/2010 | Burnes et al. |
| 2010/0114282 A1 | 5/2010 | Ebert et al. |
| 2010/0198311 A1 | 8/2010 | Sommer et al. |
| 2011/0004117 A1 | 1/2011 | Neville et al. |
| 2011/0029034 A1 | 2/2011 | Fischer et al. |
| 2012/0109237 A1 | 5/2012 | Xiao et al. |
| 2012/0130466 A1 | 5/2012 | Sommer et al. |
| 2012/0136422 A1 | 5/2012 | Ebert et al. |
| 2012/0165902 A1 | 6/2012 | Sommer et al. |
| 2012/0190991 A1 | 7/2012 | Bornzin et al. |
| 2013/0030314 A1 | 1/2013 | Keel et al. |
| 2013/0030487 A1 | 1/2013 | Keel et al. |
| 2013/0046369 A1 | 2/2013 | Eggen et al. |
| 2013/0325086 A1 | 12/2013 | Sommer et al. |
| 2015/0080981 A1 | 3/2015 | John |

OTHER PUBLICATIONS

"Vectorcardiography as a Tool for Easy Optimization of Cardiac Resynchronization Therapy in Canine Left Bundle Branch Block Hearts", by Caroline J.M. van Deursen et al., Circulation Arrhythmia and Electrophysiology, vol. 5, No. 3, Apr. 24, 2012, pp. 544-552.
C00006256.WOU2 (PCT/US2014/054971) PCT Notification of Transmittal of the International Search Report and the Written Opinion of the International Searching Authority.

* cited by examiner

FIG. 7

METHOD AND APPARATUS FOR OPTIMIZATION OF CARDIAC RESYNCHRONIZATION THERAPY USING VECTORCARDIOGRAMS DERIVED FROM IMPLANTED ELECTRODES

BACKGROUND

The present disclosure relates to implantable cardiac pulse generators (IPGs) generally, and more particularly to implantable cardioverters defibrillators (ICDs) and triple-chamber pacing devices configured to deliver cardiac resynchronization therapy (CRT).

Cardiac conduction defects and various co-morbidities of heart failure can confound the natural cardiac depolarization sequence so that upper and lower chambers fail to electrically conduct and mechanically contract during normal sinus rhythm (NSR) and/or without ventricular synchrony. In certain heart failure patients, the heart may become dilated, and the conduction and depolarization sequences of the heart chambers may, for example, exhibit inter- and/or intra-atrial conduction defects (IACD), left bundle branch block (LBBB), right bundle branch block (RBBB), and inter-ventricular conduction defects (IVCD) and the like. In patients suffering from each or a combination of such conduction defects, a lack of synchrony and/or complementary blood flow among the chambers can diminish cardiac output and impair perfusion of the organs of tissues of the patient. In addition, spontaneous depolarizations originating within the right atrium, left atrium (RA, LA), the right ventricle (RV), and/or the left ventricle (LV) can arise from diverse locations (e.g., at one or more ectopic foci) thus disturbing the natural activation sequence. Further, significant conduction disturbances between the RA and LA can result in atrial flutter or fibrillation (e.g., which can significantly impair LV filling due to the arrthymia within the LA).

It has been found that various conduction disturbances involving both bradycardia and tachycardia conditions could be overcome by applying pacing pulses at multiple electrode sites positioned in or about a single or multiple chambers of a heart in synchrony with a depolarization that is sensed at one of multiple electrode sites. It is known that cardiac output can be significantly improved when left and right chamber synchrony is restored.

Cardiac resynchronization therapy (CRT) is one of the most successful heart failure (HF) therapies to emerge in the last 25 years and is applicable to 25-30% of patients with symptomatic HF, especially those with abnormal impulse conduction through the ventricles, such as left bundle branch block (LBBB). Since initial approval of the therapy over 10 years ago, there have been hundreds of thousands of implants worldwide. Although the effects of CRT on the population level are impressive, benefits at the individual level vary considerably. Depending on the definition, the response to CRT is positive in 50-70% of patients, leaving 30-50% without significant effect. Such lack of response is especially not desirable, since CRT requires the virtually irreversible implantation of a costly device and pacing electrodes during an invasive procedure.

Effectiveness of CRT can be improved by optimal programming of the device, especially with regard to the time delay (AV-interval) between electrical stimulation of the right atrium (RA) and the ventricles and the time delay (VV-interval) between stimulation of the Right ventricle (RV) and the left ventricle (LV). Such CRT optimization increases acute hemodynamic benefits of CRT by 20-30% and improves short-term clinical response. In half of CRT clinical non-responders it is believed that symptoms could be improved by careful AV- and VV-optimization. In regular clinical practice also AV- and VV-intervals are used in the "out-of-the-box" default settings.

Echocardiographic techniques can be used to optimize AV- and VV-delays, but such optimization procedures are relatively complicated procedures and the echocardiographic measurements are notoriously inaccurate. A further serious limitation of echocardiographic optimization is that it is performed in the recumbent position in full rest, while optimization is likely more required under more conditions of higher physical activity.

The group of Prof. Prinzen has collected evidence in animal experiments and CRT patients that the QRS complex in the vectorcardiogram (VCG), measured at the body surface, provides an accurate description of the degree of resynchronization during the various AV- and VV-intervals. The results of this study are presented in "Vectorcardiography as a tool for easy optimization of cardiac resynchronization in canine LBBB hearts"; Van Deursen, et al, Circ. Arrhythm. Electrophysiol, 2012; 5:544-522, incorporated herein by reference in its entirety. This study also showed that accuracy of QRS vector determination is considerably higher than that of hemodynamic measurements.

Subsequently, in a group of 11 patients it was observed (see FIG. 1) that the best hemodynamic response ("$VTI_{LVOT}$") and the most physiological contraction pattern (minimal value of SPS+SRS) occur at AV- and VV-intervals where the three-dimensional area of the QRS-complex on the VCG loop (QRSVarea) is minimal. This minimal QRS-area, which can be determined using surface ECG measurements, provides an easy and accurate index for initial programming of optimal AV- and VV-intervals.

FIG. 1 illustrates the use of surface VCG for optimization of CRT, showing data from a representative CRT patient. The AV-delay at which QRSV area was minimal coincided with the AV-delay where a minimal value was found for the sum of septal systolic pre-stretch (SPS) and rebound stretch (SRS; indicating the least abnormal septal contraction) as well as the highest value of $VTI_{LVOT}$ (~stroke volume). In 11 patients difference between actual maximal increase in $VTI_{LVOT}$ relative to LBBB and VCG-predicted increase was small (−0.4%; IR−1.6 to 0% and −0.5%; IR−1.3 to −0.2% respectively). Surface VCGs thus provide a useful tool in conjunction with both initial implant and later follow-up visits for adjustment of stimulation parameters.

In this prior study, The Inventors also found that the measured surface QRS vector amplitude also could be used to optimize A-V and V-V delay. In this case, the combination of A-V and V-V intervals that produced a surface QRS vector amplitude halfway between that seen during LV pacing at short A-V intervals and that seen during un-paced LBBB rhythm corresponded to minimal QRSV area and to optimal hemodynamic performance.

Such optimization can be performed briefly after implantation of the CRT device. However, as the patient's disease state evolves, for example, due to an acute heart failure decompensation event or because of deleterious remodeling that occurs in the progression of heart failure or otherwise during the course of heart failure treatment and therapy, the optimal A-V and/or V-V timing may change between physician visits as well and thus would benefit from a closed loop method and apparatus for adapting to same. A similar condition may arise during physical exercise, when conduction properties of the heart may change due to activation of the sympathetic and parasympathetic nervous system.

SUMMARY OF THE INVENTION

For repetitive adjustment of AV- and VV-intervals to varying conditions (sleep, exercise, myocardial remodeling due the therapy or altering disease process) the principle of VCG optimization can be extended to a VCG derived from the implanted device and its connected electrodes rather than the body surface ECG. Such vectorcardiogam is hereafter referred to as "D-VCG" and may comprise a two-dimensional or three dimensional vectorcardiogram.

Proof of principle that these D-VCG signals can be derived from implanted electrodes and that minimal QRSVarea from D-VCG signals predicts optimal hemodynamic effect has was achieved in ten experiments in the established dog model of LBBB. In the open-chest preparation multi-electrode bands were positioned around the ventricles and an octipolar catheter was introduced in the RV.

In this model epicardial LV electrodes at the LV lateral, anterior and posterior wall were used, corresponding to locations that are achievable by using pacing leads in patients, as well as an electrode on the RV pacing electrode. From the collected electrograms 3-dimensional D-VCG-loops were constructed. From these loops QRSVarea was calculated and the values of QRSVarea were compared to hemodynamic improvements, assessed as LVdP/dtmax. Measurements were performed during 100 different combinations of atrial-RV and atrial-LV intervals. The Inventors have found that the optimal hemodynamic effect is reached at the same atrial-RV-atrial-LV interval combinations as the minimum of the QRS-Varea. The inventors consider this a strong indication that the D-VCG signal can be used to optimize AV- and VV-intervals.

An additional important benefit of the D-VCG technology is that D-VCG signals can be stored in the device and/or transmitted through remote monitoring systems, thus providing additional diagnostic information, reflecting the degree of resynchronization. Changes in the D-VCG signal can indicate loss of capture of a lead or changes in conduction within the ventricles. Moreover, the D-VCG signals can also provide accurate information on the percentage of heartbeats that are resynchronized by biventricular pacing. This percentage is especially relevant in patients with atrial fibrillation, where irregular atrial impulses may be transmitted to the ventricles without being resynchronized by concomitant, properly timed electrical stimulation. Currently devices count the number of heartbeats with biventricular pacing, but in atrial fibrillation the actual percentage of resynchronized beats can be considerably lower, as evidenced by comparisons with Holter monitoring. In a study in 19 patients Kamath et al. showed that only 9 patients had effective pacing. The other 10 patients had ~16% fusion and ~24% pseudo-fusion beats, even though the device registered >90% of heartbeats being paced. Long-term responders to CRT (defined as > or =1 New York Heart Association functional class improvement) had a significantly higher percentage of fully paced beats (86±17% vs. 66±19%; p=0.03) than nonresponders. This high percentage of not-properly resynchronized patients may also explain why the largest randomized trial evaluating the benefit of CRT in patients with atrial fibrillation (the RAFT-trial) failed to demonstrate a clear improvement. Discovery of a high percentage non-paced heartbeats by D-VCG may lead to adjustment of the therapy, for example changing medication to lower atrial rhythm or ablation of the AV-node.

DRAWINGS

FIG. 7 illustrates one example of a search according to the TSS searching methodology to identify the minimum QRS-Varea;

DESCRIPTION OF PREFERRED EMBODIMENTS

For a classical VCG ideally a perfect three-dimensional orientation of the electrodes would be desirable. However, in case of implanted pacemaker leads this is hard to achieve. Therefore the inventors investigated the prediction of the optimal AV and VV-interval with different configurations of electrodes using a canine model.

To this purpose an extensive optimization protocol was performed: 100 different combinations of atrio-RV and atrio-LV delays. These different A-V delays also provided variable V-V delays. For purpose of the invention, adjustment of A-V delays and V-V delays can be accomplished by either defining two A-V delays (e.g. A-RV and A-LV) or by defining one A-V delay and a V-V delay. Hereinafter, adjustment of A-V and V-V delays should be understood to include either approach.

In this canine model, multi-electrode bands were attached to the epicardium of the ventricles and a multi-electrode catheter was introduced in the RV. This large number of electrodes allowed testing various combinations of electrodes, mimicking possible locations of electrodes in patients.

Figure 1:
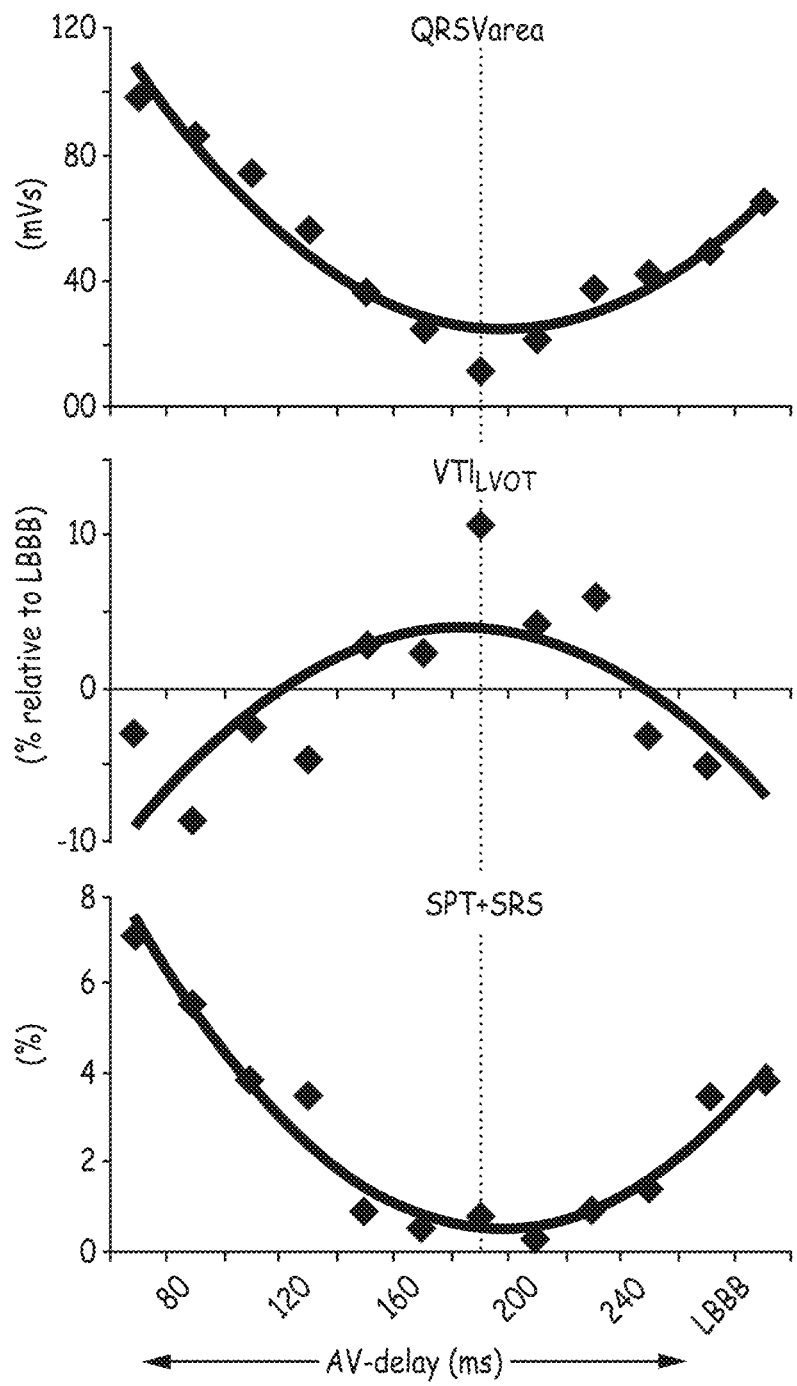
FIG. 1 illustrates results of prior testing by the inventors using surface vectorcardiograms.
Figure 2:
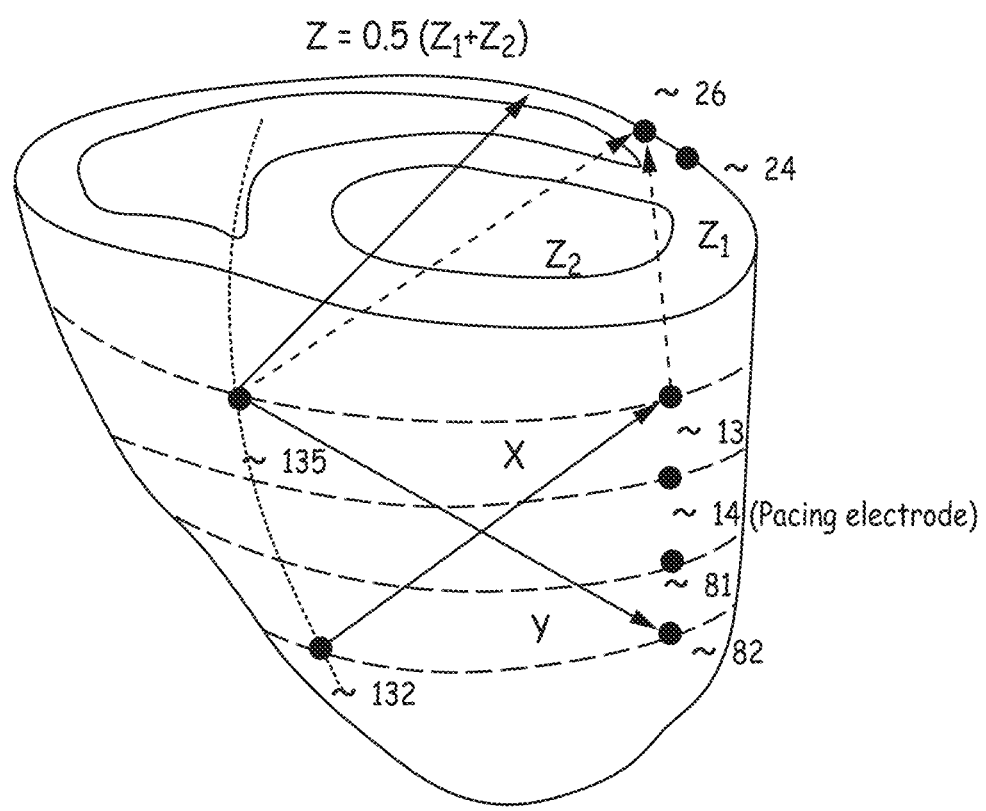
FIG. 2 illustrates locations of electrodes used in testing of vectorcardiograms (D-VCG) from implanted electrodes according to the invention.
Figure 3B:
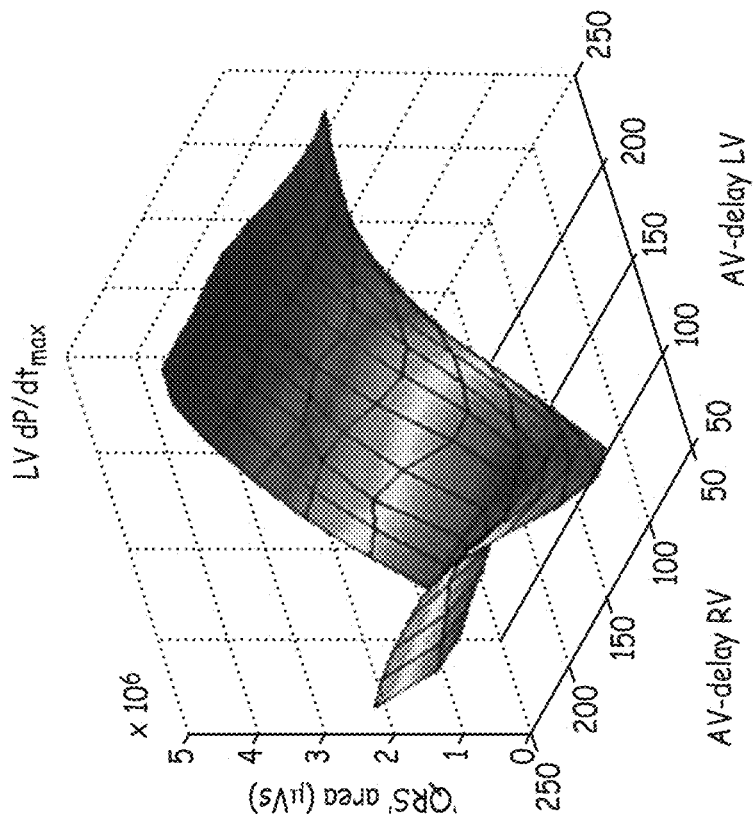
FIGS. 3A and 3B illustrate results of testing by the inventors using vectorcardiograms (D-VCG) from implanted electrodes according to the invention.
Figure 3A:
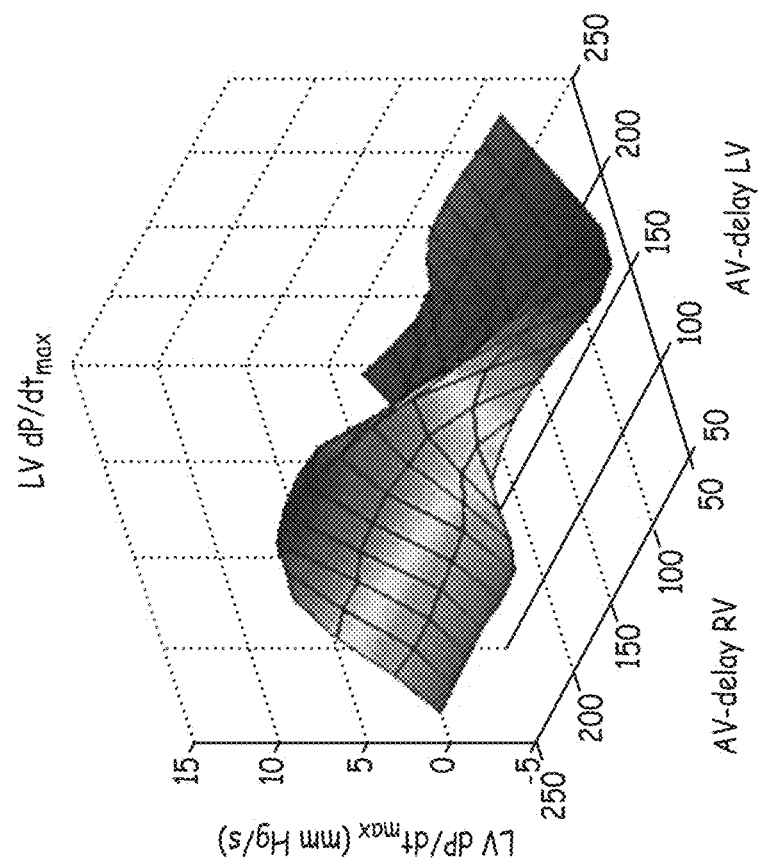

FIG. 2 illustrates the electrodes employed to obtain the D-VCG. In particular, the situation where one or two electrodes 132, 135 are positioned on the RV lead (currently already possible using the SVC coil electrode of available ICD leads) and two electrodes 13 and 82 on a Medtronic quadripolar lead was tested. For a more complete three-dimensional approach the added value of having electrodes on the part of the LV lead that is located in the proximal part of the coronary sinus was also tested using electrodes 24 and 26.

The VCG can now be reconstructed using the positions of the electrodes. For the case represented in FIG. 2 the X direction of the VCG is calculated by subtracting the signal of electrode 132 from the signal of electrode 13, the Y direction is found by subtracting the signal of electrode 135 from the signal of electrode 82 and, if employed, the Z direction can be found using the following equation:

$$Z = 0.5 * ((El_{24 \, or \, 26} - El_{135}) + (El_{24 \, or \, 26} - El_{13}))$$

From the VCG of the QRS loop, the area can be calculated. The area is defined as the area between the curve and the baseline from the beginning to the end of the QRS complex:

$$2D \; VCG: \; QRS_{perimeter} = \sum_{i=1}^{n} \sqrt{\Delta x_i^2 + \Delta y_i^2}$$

$$3D \; VCG: \; QRS_{perimeter} = \sum_{i=1}^{n} \sqrt{\Delta x_i^2 + \Delta y_i^2 + \Delta z_i^2}$$

where area, indicates the area under the ECG curve in the respective directions.

Another parameter of interest is the perimeter of the QRS loop. The QRS perimeter can be calculated in the following way:

$$2D \; VCG: \; QRS_{area} = \sqrt{QRS_{area.x}^2 + QRS_{area.y}^2}$$

$$3D \; VCG: \; QRS_{area} = \sqrt{QRS_{area.x}^2 + QRS_{area.y}^2 + QRS_{area.z}^2}$$

where $\Delta u_i = u_{i+1} - u_i$ and n is the amount of sample points in the QRS loop.

Like for the QRSVarea, also the minimum value of QRS perimeter may correspond to the largest hemodynamic response.

For each measurement, multiple beats were used. To enhance the signal to noise ratio of the VCG, an average heartbeat was calculated. It was assumed that the electrical activation is similar for every separate heartbeat. The beginning of the R-wave of each heartbeat (detected as described below) was used to align the beats. The median heartbeat was calculated in order to discard beats which were not normal (such as extrasystoles). Knowing the beginning and end of the R-wave of all heartbeats (see below), the average QRS width could be calculated and thus the beginning and end of the QRS complex of the average heartbeat is known.

The changes in LVdP/dtmax and QRS area as compared to baseline LBBB during biventricular pacing at all combinations of 10 different A-RV and 10 different A-LV delays were measured For most dogs, the minimum QRS area corresponded quite well to the maximum LV dP/dt max. A maximum in LV dP/dt max corresponded to a minimum in the VCG QRS area.

The usefulness of the QRS perimeter to predict hemodynamic changes was also tested, but the correlation between optimal hemodynamics and QRS perimeter was lower than for QRSV area.

While the specific embodiment described below focuses on QRSV area, in some patient populations, QRS perimeter or QRS vector amplitude as discussed above may also be useful in practicing the invention.

Figure 4:
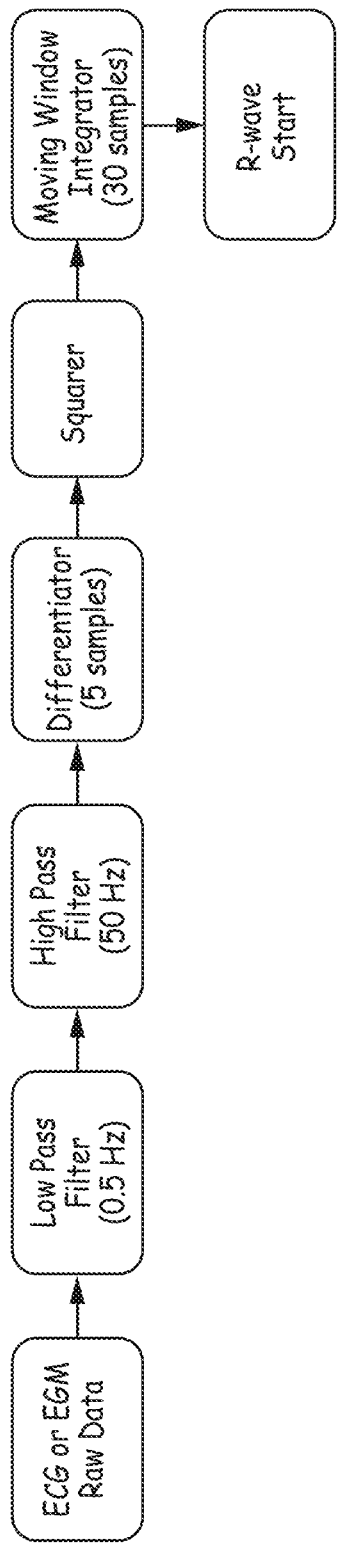
FIG. 4 illustrates the algorithm employed for determining the start of the QRS complex used in analysis of the D-VCG.
Figure 5:
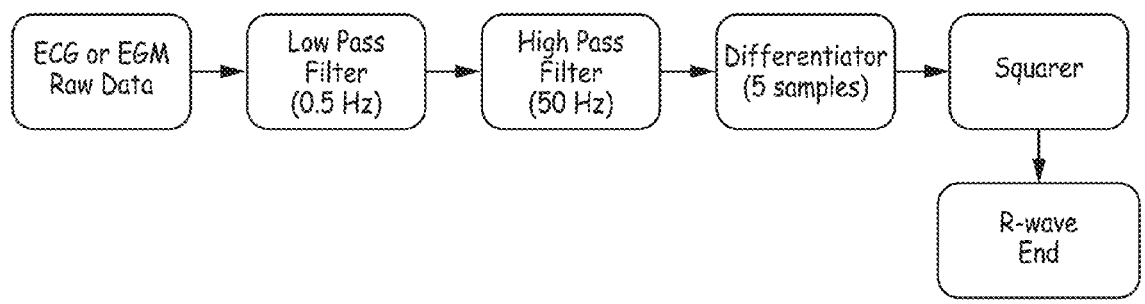
FIG. 5 illustrates the algorithm employed for determining the end of the QRS complex used in analysis of the D-VCG.

FIG. 4 and FIG. 5 illustrates the algorithms employed for automated calculation of the QRS width. According to the invention, these algorithms may be embodied in a microprocessor controlled implantable device as discussed below.

The algorithm developed for automated QRS width calculation is composed of two parts: R-wave start detection and R-wave end detection. Once the start and the end of the R-wave are located, QRS width can be calculated. Each of these parts is described in more detail bellow.

There is extensive literature related with the QRS complex detection algorithms. The inventors have selected the Pan Tompkins' algorithm for the detection of the start of the R-wave of the electrograms, because this algorithm requires minimal calculation time, which is relevant since it will be embedded in a CRT device so it is mandatory to be real time and to minimize the use of memory and CPU resources to minimize battery consumption. The algorithm can do so by performing its processing using integer arithmetic. Other known algorithms may be substituted As can be seen in FIG. 4, the input for the algorithm is the Raw ECG Data got from the leads. First, the raw ECG data should be bandpass filtered (Low Pass Filter and High Pass Filter blocks). The selected cutoff frequencies for the bandpass filtering have been 0.5 Hz for the low pass filter and 50 Hz for the high pass filter.

Once the data have been filtered a 5 sample step differentiation is applied (Differentiator block) in order to get R-wave slope information. After the differentiation the obtained signal is squared point by point (Squarer block) to make all points positive and to emphasize the higher frequencies.

Once the square signal is obtained a moving-window integration of 30 samples is put over the signal (Moving Integrator block) to obtain waveform feature information in addition to the slope of the R wave. The number of samples of the moving window is important because if the window is too wide it will merge the R-wave and T complexes together and if it is too narrow some R-waves will produce several peaks in the integration window.

When the window integration is calculated the algorithm start to look for the R-wave starts (R-wave Start Detection block). For that a threshold is calculated that is updated dynamically. The initial threshold is calculated as half of the maximum peak value in the integration window. The R-wave detection is considered when the signal crosses this threshold.

The parameters for the number of samples on the derivative and window integration part as well as the cutoff frequencies for the low and high pass filtering are set by default to:

Cutoff frequency for Low Pass Filter block=0.5 Hz
Cutoff frequency for High Pass Filter block=50 Hz
Samples for Differentiator block=5 samples
Samples for Moving Integrator block=30 samples
Nevertheless these parameters are configurable.

In the context of an implantable device according to the invention, the algorithm may be embodied, for example, in C code stored in a non-transitory form in the memory circuitry of the implantable cardiac resynchronization device.

FIG. 5 illustrates the R-wave end detection algorithm is based on the start detection algorithm so it has the same computational advantages in minimizing computing resources as the R-wave start detection process. The R-wave end detection process also takes advantage of the complex slope information obtained after the Differentiator and Squarer blocks.

As can be seen in FIG. 5 this algorithm has practically the same blocks as the one for detecting the R-wave start. The Low Pass Filter, High Pass Filter, Differentiator and Squarer blocks are exactly the same (for more information about these blocks look on the section above). The difference from the R-wave start detection algorithm is that now the Window Integrator block is not used and after the Squarer block, the end of the R-wave is found.

Once the square signal is obtained the algorithm starts to look for the R-wave end (R-wave End Detection block) based on the slope information of the squared signal. The R-wave end is detected at the end of the last peak of the squared function. An important advantage of this methodology is that for the R-wave end detection, most calculations have been already done on the R-wave start detection process, minimizing the use of computing resources.

In the context of an implantable device according to the invention, this algorithm may also be embodied, for example, in C code stored in a non-transitory form in the memory circuitry of the implantable cardiac resynchronization device.

Figure 6:
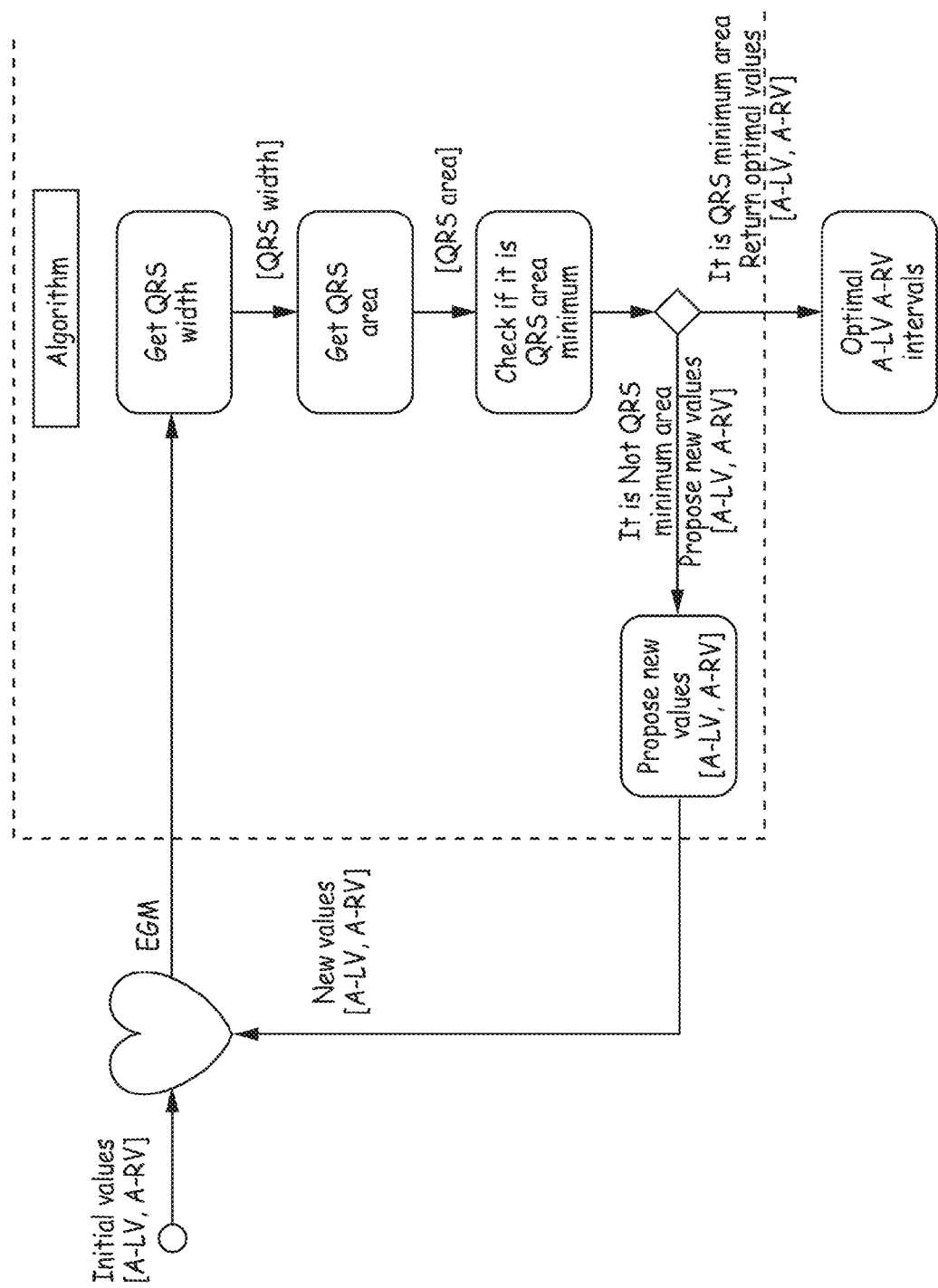
FIG. 6 illustrates the algorithm employed for identifying the minimum QRSVarea used in analysis of the D-VCG.

The algorithm for finding the minimum QRS area is illustrated in FIG. 6. The purpose of the minimum QRS area algorithm is to obtain the values of the AV and VV delays that minimize the value of QRS area. Searching for this minimum makes use of Coarse-to-Fine techniques. Within the Coarse-to-Fine searching field there are several known algorithms and techniques, including the three step search algorithms, four step search algorithms, orthogonal search algorithms and diamond search algorithms. Most of the existing algorithms on the Coarse-to-Fine area consume considerable computational resources. As commented on the section before, in the context of the invention, the algorithm is embedded in a CRT device so it is desirable to minimize the use of memory and CPU resources to minimize battery consumption. Taken this in mind the inventors have chosen the Three Step Search (TSS) algorithm as the base for the Minimum QRS Area (MQA) algorithm because of its simplicity, robustness and optimal performance. Other search algorithms may also be employed.

FIG. 6 represents the overview of the minimum QRS area algorithm. As can be seen the algorithm first obtains the value of the QRS area and thereafter determines whether it is a minimum or not. If it is not a minimum a new AV and VV delay then proposed and a new value of the QRS area is obtained. If it is a minimum then the searching is stopped and the result finalized.

In the context of an implantable device according to the invention, this algorithm may also be embodied, for example, in C code stored in a non-transitory form in the memory circuitry of the implantable cardiac resynchronization device.

Figure 7:
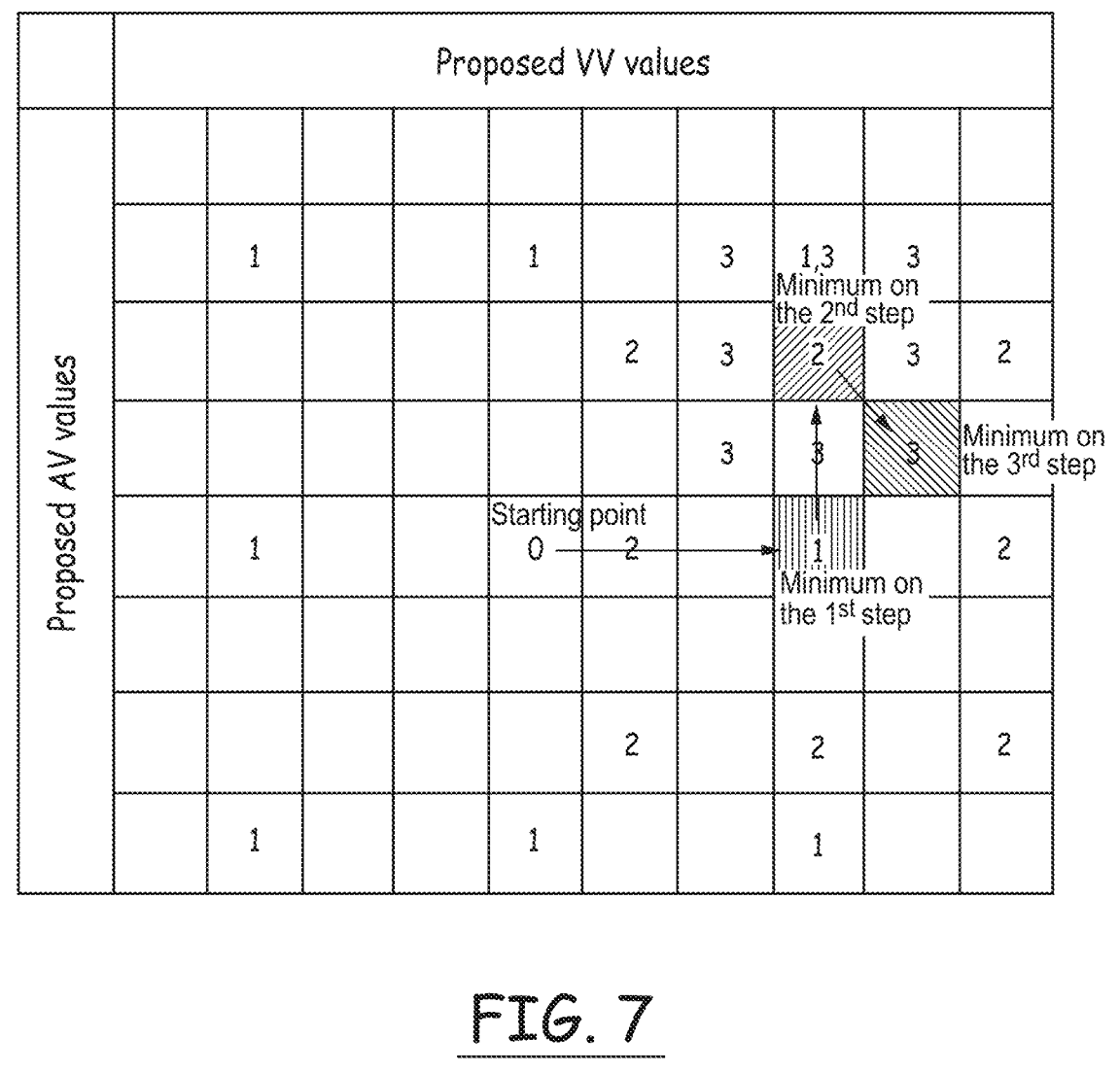

FIG. 7 illustrates one example of a search according to the TSS searching methodology.

The TSS searching algorithm proposed does a search in three steps as can be seen on FIG. 15. Below these three steps are described:

In the first step it looks for a minimum in a neighbourhood window of 3×3 cells with a time interval on AV and VV delays (programmable). Once the minimum is found look again in the neighbourhood with the same time interval on AV and VV delays. If no minimum is found then go to the second step assuming that it is the Minimum on the $1^{st}$ step (see FIG. 7).

In the second step it looks for a minimum in a neighbourhood window of 3×3 cells with a smaller time interval on AV and VV delays than in the previous step (programmable). Once the minimum is found look again in the neighbourhood with the same time interval on AV and VV delays. If no minimum is found then go to the third step assuming that it is the Minimum on the $2^{nd}$ step (see FIG. 7).

In the third step it looks for a minimum in a neighbourhood window of 3×3 cells with a smaller time interval on AV and VV delays than in the previous step (programmable). Once the minimum is found look again in the neighbourhood with the same time interval on AV and VV delays. If no minimum is found then conclude the searching with this minimum (Final minimum on FIG. 7).

The time delays for each of the steps are programmable. To test and validate the algorithm we have used a default configuration of 60 ms. on both AV and VV delays for the first step, 40 ms. for the second step and 20 ms. for the third step.

In the context of an implantable device according to the invention, this algorithm may also be embodied, for example, in C code stored in a non-transitory form in the memory circuitry of the implantable cardiac resynchronization device.

Figure 8:
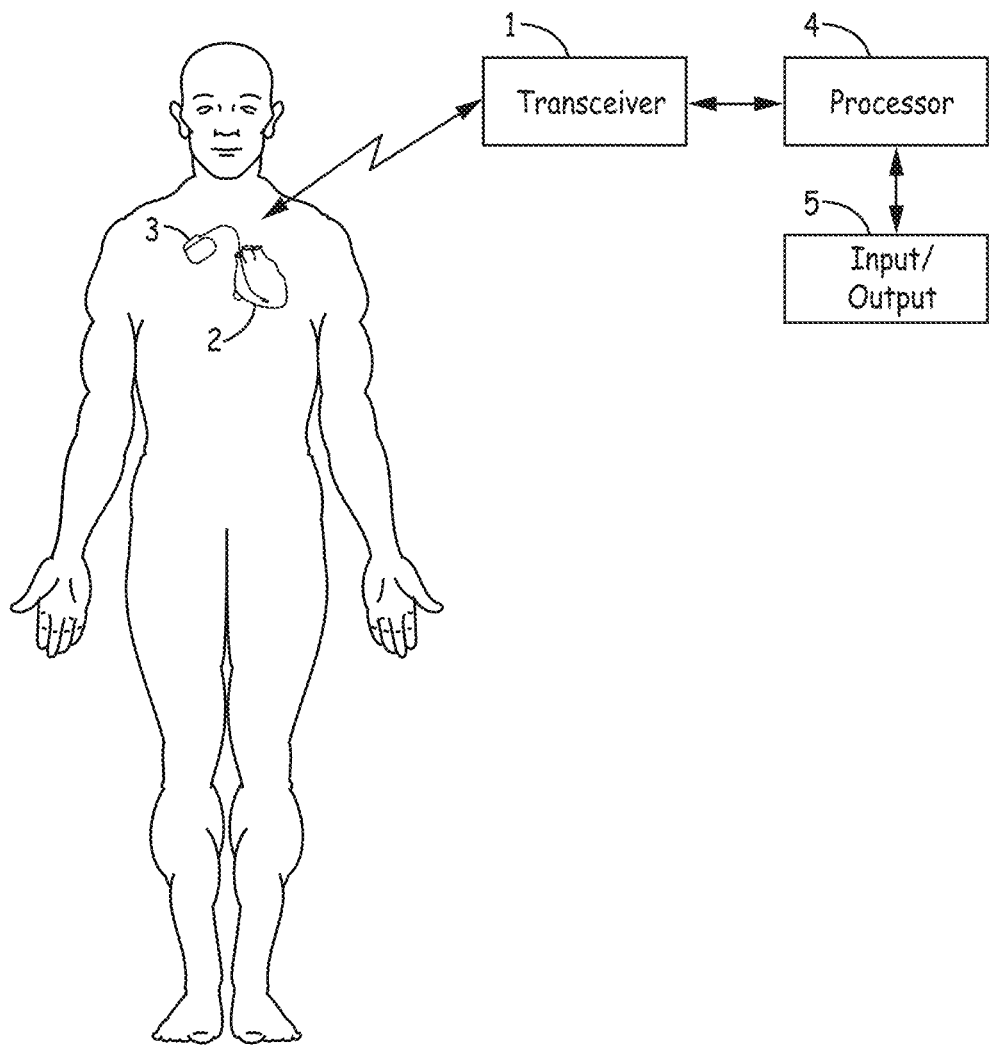
FIG. 8 shows an implanted device such as a pacemaker in an embodiment of the present invention.

Referring now to FIG. 8, a diagram is shown illustrating the environment of the apparatus and method of certain embodiments of this invention. The invention may be used with an implantable device such as a pacemaker 3, illustrated as implanted within a patient. Connected to the pacemaker is a lead 2, which extends into the patient heart, and has one or more electrodes at the distal end thereof that deliver stimulus pulses and also sense intracardiac or epicardial signals. As is well known in the pacemaker art, the sense signals can be received by the pacemaker, digitized and stored in memory, for later transmission to an external device; alternately, they can be downloaded directly to an external programmer device. Likewise, one or more sensors located on the lead or in the pacemaker can produce the signals that are to be digitized and stored. As shown, the transceiver 1 may be a conventional programmer as used in the pacemaker art. The programmer, when it has received data from the pacemaker, can transfer it to a processor 4, which in turn can output data to input/output device 5, all in a well-known manner.

Figure 9:
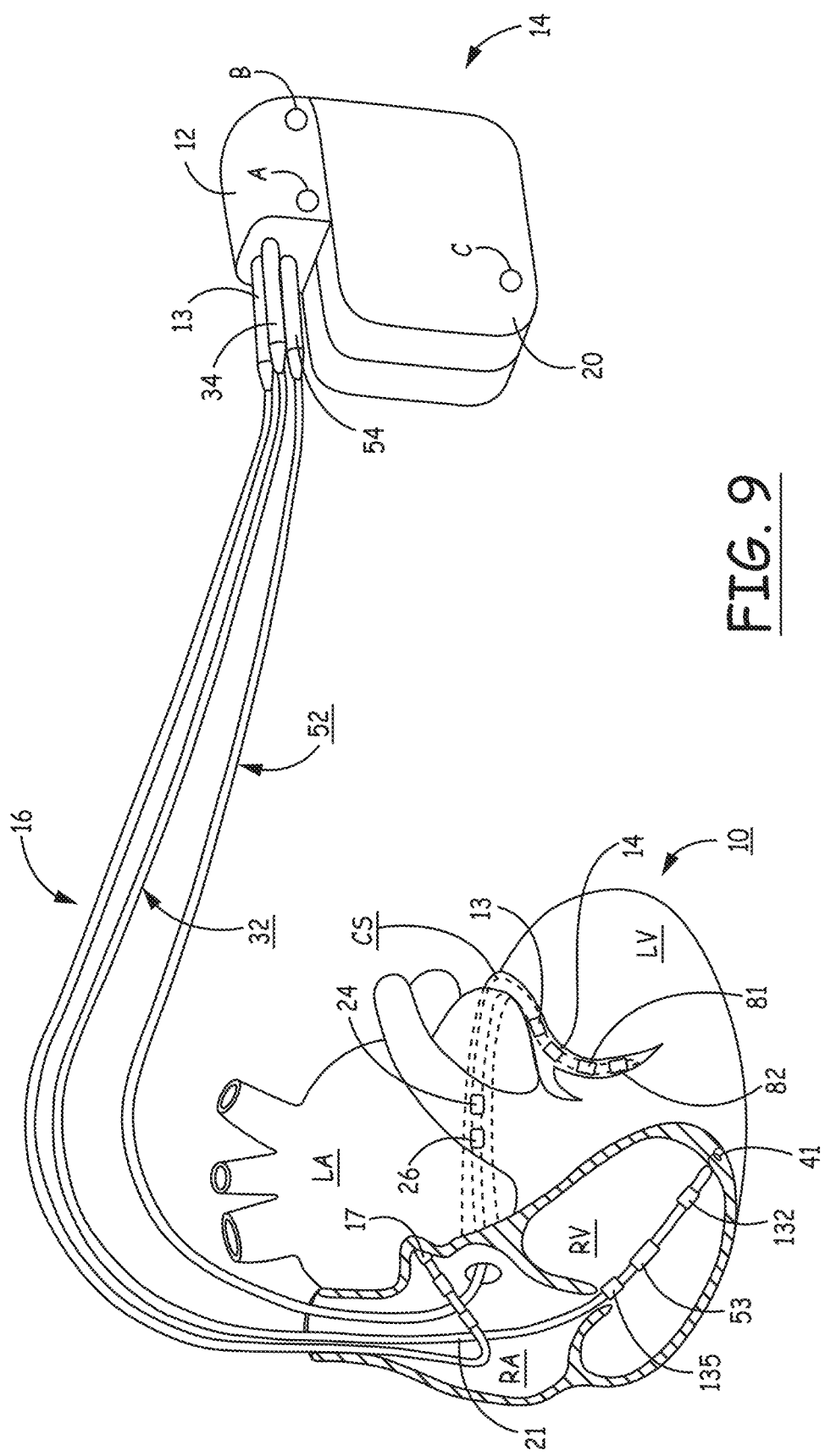
FIG. 9 is a diagram illustrating an implanted device system of the general type in which the invention may be embodied.

FIG. 9 depicts an implanted, multi-channel cardiac pacemaker, ICD, IPG (implantable pulse generator) or other IMD of the above noted types for restoring A-V synchronous contractions of the atrial and ventricular chambers and simultaneous or sequential pacing of the right and left ventricles. The pacemaker IPG 14 is implanted subcutaneously in a patient's body. Endocardial leads 16, 32, and 52 connect the IPG 14 with the RA, the RV and the LV, respectively. Each lead includes electrical conductors and pace/sense electrodes. A remote indifferent can electrode 20 may be formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

Figure 11:
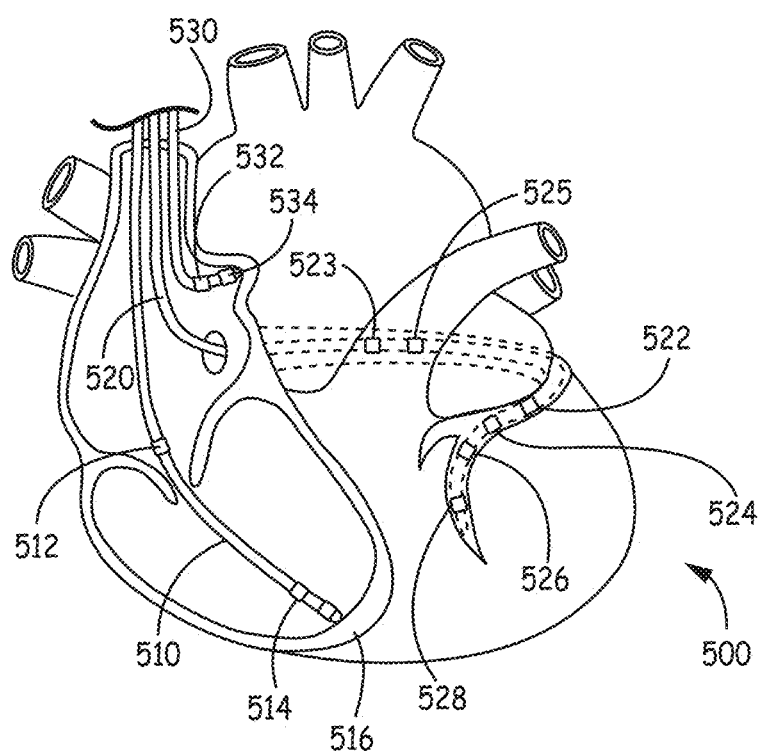
FIG. 11 is a diagram depicting one particular set of electrodes and leads that may be used to practice the present invention.

A more specific set of electrodes and leads for use in conjunction with the present invention is illustrated in FIG. 11

The endocardial RV lead 32 is passed through a vein into the RA chamber of the heart 10, and the distal end of the RV lead 32 is attached to the RV wall by an attachment mechanism 41. The endocardial RV lead 32 is formed with an in-line connector 34 fitting into a bipolar bore of IPG connector block 12 that is coupled to electrically insulated conductors within the lead body and connected with the electrodes thereon. In the case in which the electrode configuration of FIG. 2 is employed, lead 32 would carry electrodes 135 and 132. Additional electrodes may be provided as discussed below in conjunction with FIG. 11.

Delivery of atrial pacing pulses and sensing of atrial sense events is effected using lead 16, by means of the distal tip RA pace/sense electrode 17 and proximal ring RA pace/sense electrode 21, wherein the proximal ring RA pace/sense electrode 21 functions as an indifferent electrode (IND_RA). The endocardial RV lead 16 is formed with an in-line connector 13 fitting into a bipolar bore of IPG connector block 12 that is coupled to electrically insulated conductors within the lead body and connected with the electrodes thereon.

Lead 52 may be a multi-electrode endocardial lead passed through the right atrium, through the coronary sinus and into the great cardiac vein. In the case in which the electrode configuration of FIG. 2 is employed, lead 52 would carry electrodes 13, 14, 81, 82, and, if present, electrodes 24 and 26 (all illustrated in FIG. 2). Additional electrodes may be provided as discussed below in conjunction with FIG. 9. The endocardial RV lead 52 is formed with an in-line connector 54 fitting into a bipolar bore of IPG connector block 12 that is coupled to electrically insulated conductors within the lead body and connected with the electrodes thereon.

Also depicted in FIG. 9 is an optional RV sensor 53 and an optional LV sensor 57 which each may comprise one or more of a variety of sensors as is known in the art. Preferably RV sensors 53 and/or 57, if present, comprise absolute pressure sensors, but other pressure sensors may be utilized. In addition or as an alternative, sensors 53 and 57 may comprise accelerometers, impedance electrodes, saturated oxygen sensors, pH sensors, or the like. Of course, such sensors must be rendered biocompatible and reliable for long-term use. In addition, one or more sensors may be disposed in or on the housing 20 of IMD 14 such as sensors A, B, or C depicted in FIG. 9.

Figure 10:
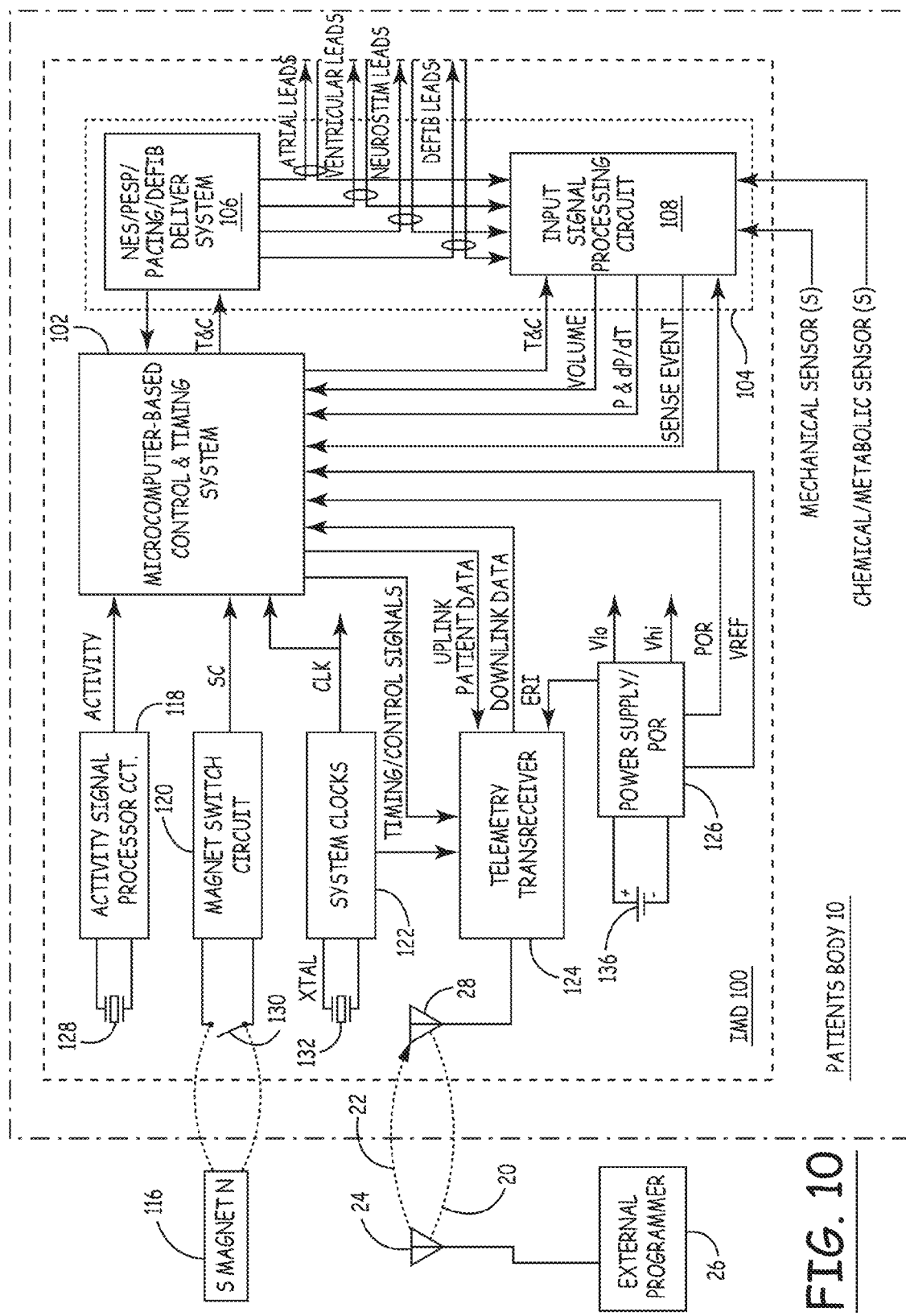
FIG. 10 is a schematic diagram depicting a multi-channel, atrial and bi-ventricular, monitoring/pacing implantable medical device (IMD) of the general type in which embodiments of the invention are preferably implemented.

FIG. 10 depicts a system architecture of an exemplary multi-chamber IMD 100 implanted into a patient's body 10 that provides delivery of a therapy and/or physiologic input signal processing. The typical multi-chamber monitor/sensor 100 has a system architecture that is constructed about a microcomputer-based control and timing system 102 that varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU, ALU, etc., of a typical microprocessor core architecture. Of course, such firmware and software may be modified in situ (e.g., in vivo) and the operational characteristics may be adapted for a particular situation or patient. A physician or clinician may change one or more parameters that will cause a change in the detection or response of such algorithms. Discrete values may be changed such that a desired software routine is advantageously altered, although sometimes an entirely new set of operating software may be substituted for an existing set of operating software, as is known in the art. The microcomputer-based multi-chamber monitor/sensor control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor 100 can be accomplished with dedicated circuit hardware or state machine logic rather than a programmed microcomputer.

The multi-chamber monitor/sensor 100 also typically includes patient interface circuitry for receiving signals from sensors and pace/sense electrodes located at specific sites of the patient's heart chambers and/or delivering stimulation to derive heart failure parameters or a pacing therapy to the heart chambers. The patient interface circuitry therefore comprises a stimulation delivery system 106 optionally including pacing and other stimulation therapies and a physiologic input signal processing circuit 108 for processing the blood pressure and volumetric signals output by sensors. For purposes of illustration of the possible uses of these embodiments of the invention, a set of lead connections are depicted for making electrical connections between the therapy delivery system 106 and the input signal processing circuit 108 and sets of pace/sense electrodes located in operative relation to the RA, LA, RV and LV.

The physiologic input signal processing circuit 108 therefore includes at least one electrical signal amplifier circuit for amplifying, processing and in some cases detecting sense events from characteristics of the electrical sense signal or sensor output signal. The physiologic input signal processing circuit 108 in multi-chamber monitor/sensors providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave, R-wave, or T-wave respectively and providing an ASENSE, VSENSE or TSENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in a variety of ways known in the art. In addition, the input signal processing circuit 108 includes at least one physiologic sensor signal-processing channel for sensing and processing a sensor derived signal from a physiologic sensor located in relation to a heart chamber or elsewhere in the body.

Telemetry circuit receives and transmits signals 20 and 22 to and from an external programmer 26 via antennas 24 and 28. Programming information regarding device settings, including software for use by microcomputer 102 may be received from the External programmer 26. The information received may include portions of the stored programming information embodying the QRS area calculation methodology discussed above, as well as control parameters for controlling general device operation as is well known to the art. The results of analysis of the D-VCG according to the present invention may correspondingly be transmitted to the external programmer 26 for the use of the physician.

Power is typically provide by a battery 136 and a regulated power supply 126. Timing is controlled by a system clock using crystal oscillator 132. An externally applied magnet 116 may be used in conjunction with reed switch 130 and associated circuitry 120 to enable receipt of near-field telemetry and/or to temporarily alter the operation of the device as known to the art.

An activity sensor 128 and associated circuitry 118 may be employed to provide a signal to processor 102 allowing it to regulate pacing rate as a function of detected physical activity. Other mechanical or chemical sensors, e.g. sensors 47 and 53 as discussed above in conjunction with FIG. 9 may also be employed.

FIG. 11 illustrates a heart 500 and one set of leads and electrodes that may be employed in conjunction with the present invention. Ventricular lead 510 carries electrodes 512, 514 and 516. In conjunction with measurement along the X axis as illustrated in FIG. 2, electrodes 514 and 522 may be employed. In conjunction with measurement along the Y axis, electrodes 512 and 528 may be employed. In conjunction with measurement along the Z axis, if employed, electrodes 512 and 522, 523 or 525 may be used. Sensing and pacing of the left ventricle may be performed using electrodes 524 and 526, which may take the form of a closely spaced bipolar pair.

Sensing and pacing of the right ventricle may be performed using electrode 516 in conjunction with a remote indifferent electrode or in conjunction with an additional electrode on lead 510. Atrial pacing and sensing are done using electrodes 532 and 534 on lead 530 and 526, which may take the form of a closely spaced bipolar pair.

During the procedure for measuring the D-VCG and optimizing the V-V and A-V intervals, it is generally preferred to pace using electrodes that are not being employed to measure the D-VCG. Other electrode configurations may be substituted. Particularly in the case of devices that include defibrillation capabilities, one or more of the electrodes employed to measure the D-VCG may be defibrillation electrodes. If a sufficient number of electrodes are available, the physician may be able to select which electrodes are employed to perform the various functions.

Figure 12:
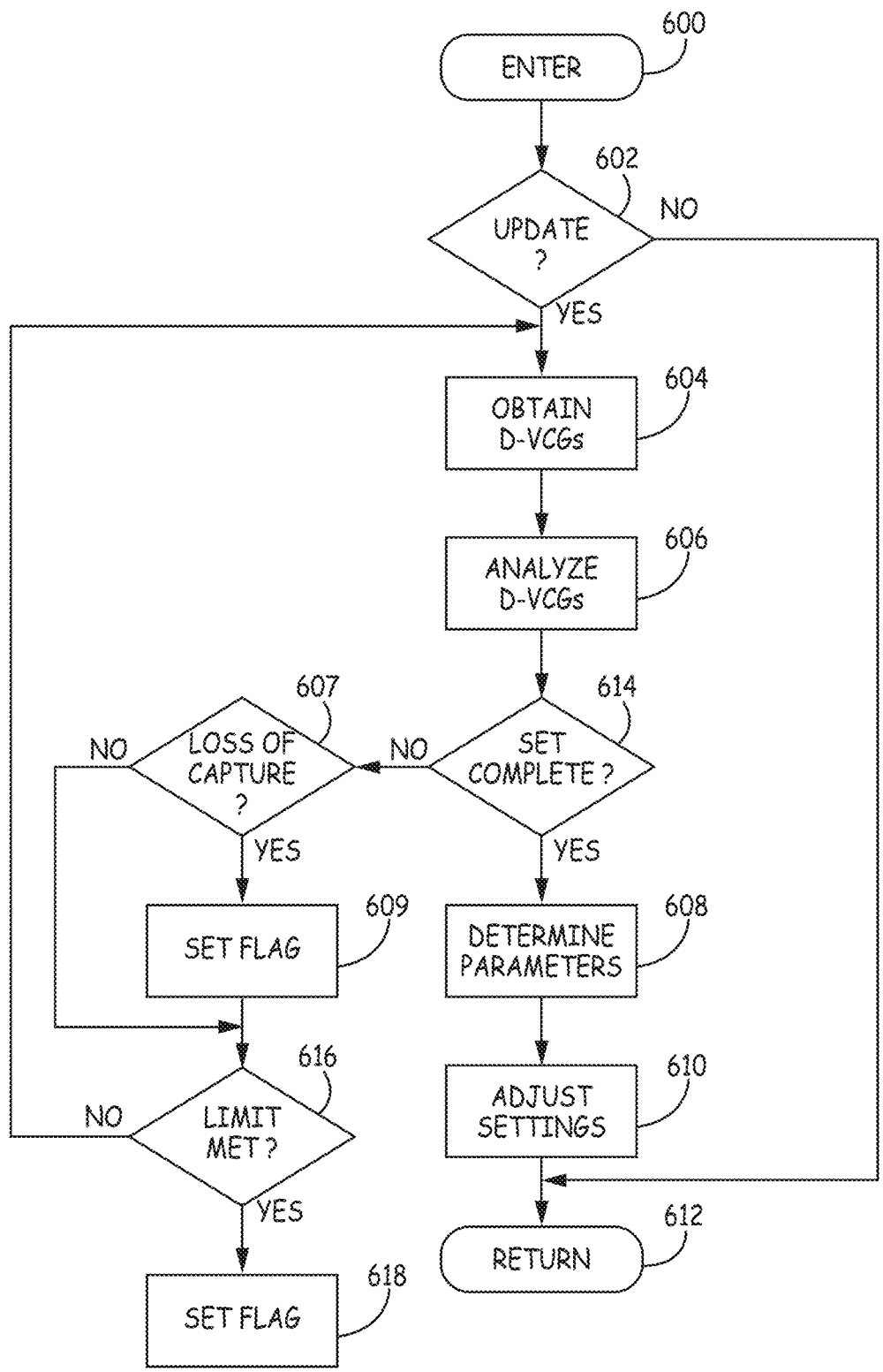
FIG. 12 is a flow-chart illustrating operation of a device according to one embodiment of the present invention.

FIG. 12 is a flow-chart illustrating operation of the D-VCG analysis methodology as performed by the microprocessor 102 under control of corresponding programmed instructions stored in memory associated therewith. The process, for example, may be interrupt driven and entered at 600 responsive to delivery of a ventricular pacing pule or sensing of a ventricular depolarization. The processor checks at 602 to determine whether an update of the D-VCG analysis is desirable. This may occur after expiration of pre-set time periods or in response to other events such as detection of termination of a tachyarrhythmia, the end of a programming session or the like. If the D-VCG analysis is due for updating, the microprocessor controls the output circuitry 106 (FIG. 9) to deliver atrial and ventricular pacing pulses at varying A-V and V-V intervals as discussed above. Resulting sensed signals along the X- and Y-axes, and along the Z-axis if used, are stored in memory for later analysis.

Analysis of the D-VCG signals at 606 includes identifying the start and end points of the QRS complexes and calculation of the QRSVareas between the start and end points as described above.

The processor then checks at 614 to determine whether a complete set of D-VCG has been obtained for the available A-V and V-V intervals settings. If so, the processor proceeds to determine the optimal A-V and V-V settings as discussed above. If not, the processor checks at 616 to determine whether a maximum number of delivered pacing pulses or a maximum time interval for collection of D-VCGs has been reached. If the limit has been reached, this may indicate that the D-VCG measurement process is no longer producing useful results. If so, the processor may set a flag so indication at 618 and the device may return to normal operation without adjusting the A-V and/or V-V intervals. The processor may optionally trigger an alert or store information for later transmission to an external programmer.

Analysis may conveniently also be used to detect losses of capture at 607. If the percentage or number of pacing pulses which are accompanied by loss of capture exceeds a pre-set threshold at 607, a flag may be set at 609 and the stored information related to loss of capture may be later telemetered to an external programmer or an alert may be generated to facilitate consideration of a change in the type of therapy being delivered, as discussed above.

Assuming that the D-VCG signals stored in memory are sufficient to determine an optimal D-VCG at 614, the search methodology described above is employed to select new optimal A-V and/or V-V interval values as described above. The device then returns to normal operation at with the A-V and/or V-V intervals as adjusted at 610.

While the above description is based upon the assumption that the device is operating as a bi-ventricular pacer, it is believed that the basic methodology of the invention may also be applied to devices operating in a fusion pacing mode in which only the left ventricle is paced. In such cases, the device would measure the RA to RV conduction time rather than control it by means of an RA-RV pacing interval. The measured RA-RV interval would be used to allow the device to scan through either the available A-LV intervals. In such case, the minimal QRSVarea may correspondingly be employed to determine an optimal a-LV pacing interval.

Further, while the above description focuses on use of the minimum QRSV area as a preferred metric for identifying optimal V-V and A-V pacing interval, in some groups of patients, minimum QRS perimeter or QRS vector amplitude as discussed above may be substituted in the methodology as otherwise described.

The invention is also believed to be useful in the selection if appropriate locations for pacing electrodes used to provide CRT pacing. In such cases, during initial implant, the optimization methodology discussed above may be iteratively performed with the relevant RV and LV electrodes located at different sites. Based upon the results, the physician may choose a preferred set of locations for initial implant. Further, as the number and locations of electrodes increases, there will be circumstances in which the selection of which electrodes to be used for pacing will also be adjustable after implant. In these cases, as with initial implant, iterative application of the methodology herein to the available pacing electrode configurations may also be performed.

In either case, it is anticipated that the physician will want to review the results for the various electrode configurations available and make his or her own judgment as to which configuration should be employed. However, it is also within the scope of the invention that the device itself may periodically test the available configurations and either recommend a preferred configuration or select a preferred configuration automatically as part of steps 608 and 610 in FIG. 12.

One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A method of adjusting a cardiac resynchronization (CRT) pacemaker of the type having the capabilities of left ventricular pacing and atrial sensing, comprising:
   automatically deriving a vectorcardiogram from implanted electrodes (D-VCG) by a processor of the pacemaker;
   analyzing the D-VCG by the processor;
   deriving optimal CRT pacing parameters from the analysis of the D-VCG; and
   adjusting the CRT pacemaker according to the derived parameters; and
   employing the obtained D-VCG to detect loss of capture, due to technical failure of the pacemaker or lead, irregular heart beats or altering cardiac conduction properties.

2. A method according to claim 1 further comprising storage of the D-VCG for diagnostic purposes.

3. A method according to claim 1, wherein the derived pacing parameters include an atrial to left ventricular (A-LV) and an atrial to right ventricular (A-RV) pacing interval.

4. A method according to claim 1, wherein the derived pacing parameters include an atrial to left ventricular (A-LV) pacing interval.

5. A method according to claim 1 wherein the derived parameters include an optimal electrode location.

6. A method according to claim 1 wherein the analysis of the D-VCG comprises measurement of QRS vector area (QRSVarea).

7. A method according to claim 6 wherein the optimal pacing parameters comprise those that result in a minimum QRSVarea.

8. A method according to claim 1 wherein the analysis of the D-VCG comprises measurement of QRS vector perimeter.

9. A method according to claim 1 wherein the analysis of the D-VCG comprises measurement of QRS vector amplitude.

10. A method according to claim 1 wherein analysis of the D-VCGs comprises identification of start and endpoints of QRS complexes.

11. A method according to claim 1 wherein the analysis of D-VCGs comprises performing the analysis in conjunction with delivery of CRT pacing using different pacing parameters.

12. A method according to claim 1 wherein the analysis of D-VCGs comprises performing the analysis in conjunction with delivery of CRT pacing using different pacing electrode configurations.

13. A cardiac resynchronization (CRT) pacemaker of the type having the capabilities of left ventricular pacing and atrial sensing, and comprising a set of implanted electrodes, comprising:
a processor configured to:
 a) derive a vectorcardiogram from the implanted electrodes (D-VCG);
 b) analyze the D-VCG;
 c) derive optimal CRT pacing parameters from the analysis of the D-VCG; and
 d) control delivery of CRT pacing according to the derived parameters;
wherein the processor is further configured to derive the D-VCG by:
 determining a first axis signal of the D-VCG between a first electrode and a second electrode of the set of implanted electrodes; and
 determining a second axis signal of the D-VCG between a third electrode and a fourth electrode of the set of implanted electrodes;
wherein the processor is configured to analyze the D-VCG by computing a QRS parameter using the first axis signal and the second axis signal; and
wherein the processor is further configured to derive the D-VCG by
 determining a first vector signal between the first electrode and a fifth electrode of the set of implanted electrodes;
 determining a second vector signal between the third electrode and the fifth electrode; and
 determining a third axis of the D-VCG as a combination of the first vector signal and the second vector signal; and
wherein the processor is configured to analyze the D-VCG by computing the QRS parameter using the first axis signal, the second axis signal and the third axis signal.

14. A CRT pacemaker according to claim 13 further comprising memory configured to store the D-VCG for diagnostic purposes.

15. A CRT pacemaker according to claim 13, wherein the derived pacing parameters include an atrial to left ventricular (A-LV) and an atrial to right ventricular (A-RV) pacing interval.

16. A CRT pacemaker according to claim 13, wherein the derived pacing parameters include an atrial to left ventricular (A-LV) pacing interval.

17. A CRT pacemaker according to claim 13 wherein the derived parameters include an optimal electrode location.

18. A CRT pacemaker according to claim 13 wherein the analysis of the D-VCG comprises measurement of QRS vector area (QRSVarea).

19. A CRT pacemaker according to claim 18 wherein the optimal pacing parameters comprise those that result in a minimum QRSVarea.

20. A CRT pacemaker according to claim 13 wherein the analysis of the D-VCG comprises measurement of QRS vector perimeter.

21. A CRT pacemaker according to claim 13 wherein the analysis of the D-VCG comprises measurement of QRS vector amplitude.

22. A CRT pacemaker according to claim 13
wherein analysis of the D-VCGs comprises identification of start and endpoints of QRS complexes.

23. A CRT pacemaker according to claim 13 wherein the analysis of D-VCGs comprises performing the analysis in conjunction with delivery of CRT pacing using different pacing parameters.

24. A CRT pacemaker according to claim 13 wherein the analysis of D-VCGs comprises performing the analysis in conjunction with delivery of CRT pacing using different pacing electrode configurations.

25. A cardiac resynchronization (CRT) pacemaker of the type having the capabilities of left ventricular pacing and atrial sensing, and comprising a set of implanted electrodes, comprising:
a processor configured to:
 a) derive a vectorcardiogram from the implanted electrodes (D-VCG);
 b) analyze the D-VCG;
 c) derive optimal CRT pacing parameters from the analysis of the D-VCG; and
 d) control delivery of CRT pacing according to the derived parameters; and
employing the obtained D-VCG to detect loss of capture, due to technical failure of the pacemaker or lead, irregular heart beats or altering cardiac conduction properties.

* * * * *